(12) United States Patent
Davies et al.

(10) Patent No.: US 9,204,799 B2
(45) Date of Patent: Dec. 8, 2015

(54) PRESSURE SENSOR

(75) Inventors: Roy Frederick Davies, Oxon (GB);
Ejaz Huq, Oxon (GB); Stephen George Edward Barker, Surrey (GB)

(73) Assignee: SFH OXFORD LIMITED, Oxon (GB)

( * ) Notice: Subject to any disclaimer, the term of this patent is extended or adjusted under 35 U.S.C. 154(b) by 216 days.

(21) Appl. No.: 13/977,385

(22) PCT Filed: Jan. 5, 2012

(86) PCT No.: PCT/GB2012/050012
§ 371 (c)(1),
(2), (4) Date: Sep. 13, 2013

(87) PCT Pub. No.: WO2012/093259
PCT Pub. Date: Jul. 12, 2012

(65) Prior Publication Data
US 2013/0345598 A1    Dec. 26, 2013

(30) Foreign Application Priority Data
Jan. 5, 2011   (GB) .................................. 1100096.5

(51) Int. Cl.
*A61B 5/117*  (2006.01)
*A61B 5/103*  (2006.01)
*A61B 5/00*  (2006.01)
*A61F 13/00*  (2006.01)

(52) U.S. Cl.
CPC ................ *A61B 5/0053* (2013.01); *A61F 13/00* (2013.01); *A61B 2562/0247* (2013.01); *A61F 2013/00957* (2013.01)

(58) Field of Classification Search
CPC ........................................................ A61B 5/0053
USPC ...................... 600/587; 73/862.621, 862.624, 73/862.626, 862.627; 602/13
See application file for complete search history.

(56) References Cited

U.S. PATENT DOCUMENTS 5,838,244 A    11/1998    Schmidt

FOREIGN PATENT DOCUMENTS

IE    84492  B1    2/2007

*Primary Examiner* — Brian Szmal
(74) *Attorney, Agent, or Firm* — Saliwanchik, Lloyd & Eisenschenk

(57) ABSTRACT

A sensor suitable for measuring the pressure applied by a bandage, the sensor being in the form of an elongate strip having a plurality of pads arranged along its length, wherein the sensor includes a connection to each pad, whereby the pressure applied to each pad can be determined independently, wherein each pad is inflatable to form an expanded pad protruding above the surface of the strip, and deflatable so that it does not impede removal of the sensor from the bandage. Such a sensor is primarily intended for single use, i.e. is disposable.

8 Claims, 2 Drawing Sheets

PRESSURE SENSOR

CROSS REFERENCE TO A RELATED APPLICATION

This application is a National Stage Application of International Application Number PCT/GB2012/050012, filed Jan. 5, 2012; which claims priority to Great Britain Application No. 1100096.5, filed Jan. 5, 2011; which are incorporated herein by reference in their entirety.

FIELD OF THE INVENTION

This invention relates to a sensor, and in particular to a device that can be used to measure pressure applied by a bandage or stocking around a leg ulcer.

BACKGROUND OF THE INVENTION

Venous leg ulcers affect between 1% and 1.5% of the UK population at any given time. Based on 60 million persons, this equates to approximately 200,000 with ulcers requiring treatment. Estimates of cost to treat range from £450 million to £800 million per year. In the USA, the estimate of cost to treat comes in at almost $5 billion per year. The average length of time any one person has an ulcer for is upwards of two years. If an ulcer does heal, relapse rates are as high as 50% at six months, without precautionary measures.

A mainstay of treatment is multi-layered graduated compression bandaging; using an elasticated bandage, higher pressure is exerted at the ankle, the bandage becoming progressively less compressive up to the knee. Bandaging up beyond the knee is not necessary. The application of excessive pressure can cause discomfort or harm to a patient. The application of insufficient pressure has negative consequences on the healing process, and may also provide insufficient support or fail to maintain the bandage in place. Accordingly, there is a need to apply correct graduated compression. This is a highly skilled task, e.g. requiring nurses to undertake training courses. Health care practitioners generally become competent only through years of experience.

Many compression bandage types exist on the market, all with different stretch characteristics, and many techniques for application exist. These factors make it exceptionally difficult to get the graduated compression profile absolutely correct, so as to maximise the chance that the ulcer eventually heals.

Individual diaphragm pressure sensors are well known and can be air-filled, water-filled, oil-filled, etc. Commercially available rigs for noting the compression ability of graduated compression socks on, for example, a test mannequin are based on a diaphragm system. However, the problem of ensuring correct usage remains.

WO2006/013422 reviews known pressure sensors, and proposes a sensor that may be placed directly on the body or between the windings of a bandage. Such a pressure sensor, for providing an indication of the pressure applied by a bandage to a human or animal body, comprises an elongate, flexible support strip adapted to be placed between a bandage and the body, the strip carrying a flat pressure-sensitive portion whose electrical properties vary with applied pressure normal to the plane of the strip, and also carrying flat, flexible conductors for connecting the pressure-sensitive portion to a supply of electricity and to means for providing an indication of the applied pressure. The pressure-sensitive portion is a Quantum Tunnelling Composite (QTC), a material available in flexible form as sheets and whose conductivity changes in accordance with pressure applied across the plane of the sheet.

The use of a flat pressure-sensitive portion allows the provision of a thin strip that can be readily introduced underneath or between the windings of a bandage, and can also be removed after use. The device is however dependent on the use of a QTC material, and has disadvantages including (i) the difficulty of producing a homogeneous composite material such that the electrical response is uniform throughout the device, and (ii) the fact that the magnitude of the obtained signal from such a sensor may be low and also compromised by the level of noise, and (iii) the likelihood that incorrect measurement will be recorded if the bandage is pulled laterally across the device. In addition, if a raised area is used to obtain good results, it may be difficult to remove the device from a bandage. Furthermore, the device may be uneconomical as a single-use, disposable product.

SUMMARY OF THE INVENTION

The present invention is based on a realisation of the need for a simple, single-use, disposable device that can aid in the placement of graduated compression bandages, to readily achieve a correct compression profile up the leg.

According to one aspect of the present invention, a pressure sensor comprises an elongate strip having a plurality of pressure-sensing pads arranged along its length, the strip further comprising an independent connection to each pad, whereby the pressure applied to each pad can be determined independently. In particular, a characteristic feature of the present invention is that each pad is inflatable to form an expanded pad or dome protruding above the surface of the strip, and deflatable. Deflation can be achieved by the application of negative pressure that can be maintained during withdrawal. This means that a dome formed by inflation can be drawn down and held below the upper surface of the strip, so that it does not impede removal of the sensor from an applied bandage.

According to a second aspect of the present invention, a method for indicating the pressure applied by the bandage to a human or animal body, and in particular to a limb, comprises positioning a sensor between a bandage and the body, wherein the sensor is in the form of an elongate strip having a plurality of pressure-sensing pads arranged along its length, wherein the sensor includes a connection to each pad, wherein each pad is inflatable to form an expanded pad or dome protruding above the surface of the strip, and deflatable so that it does not impede removal of the sensor from the bandage, and determining the pressure applied to each pad.

Yet another aspect of the present invention is a method of applying a bandage to a human or animal body, and in particular to a limb thereof, in which an indication of the pressure applied by the bandage to the body is provided, and the bandage is applied in such a way that the applied pressure is maintained within predetermined limits. The method comprises positioning a sensor between a bandage and the body, wherein the sensor is in the form of an elongate strip having a plurality of pressure-sensing pads arranged along its length, wherein the sensor includes a connection to each pad or dome, wherein each pad is inflatable to form an expanded pad protruding above the surface of the strip, and deflatable so that it does not impede removal of the sensor from the bandage, and determining the pressure applied to each pad.

A device of the invention can provide one or more of various advantages. It can be applicable to all shapes and lengths of leg, easy to use, give an accurate pressure profile over a range of compression levels, respond to pressure changes quickly and accurately, be easily removed, and be economic to produce. It can make the process of graduated compression bandaging sufficiently straightforward that prolonged training in the technique is not necessary. Anyone from health care assistant up to consultant surgeon could use the device to achieve a correct technique in moments.

It will be readily appreciated that a sensor of the present invention provides many of the characteristics and advantages described for the device disclosed in WO2006/103422. It will often be preferred to obtain accurate and true measurements. However, it is however more economical to produce and also can be more sensitive. It is important to bear in mind that it may not be necessary to provide an absolute measure of the pressure applied to each pad; rather, when connected to means of determining and preferably also displaying the pressure applied to each pad, relative pressures only are needed, in order to achieve effective graduated compression.

DESCRIPTION OF PREFERRED EMBODIMENTS

A preferred embodiment of the invention is a single-use, disposable product that is placed along the inside aspect of the leg (from the ankle to well above the knee) at the time of graduated compression bandaging being applied. Along its length, there are, for example, 4 to 8, e.g. 6 pressure sensors. These may be based on air-filled diaphragms. A sensor of the invention may be constructed of any suitable substrate material, e.g. plastics, ceramic or metal. The material is preferably flexible, to conform to the shape of the leg.

The length and width of a device of the invention are not critical. These dimensions may be, for example, 400 mm long and 30 mm wide.

A sensor of the invention (when deflated) should be as thin as is reasonably practicable for easy removal. Depending on the materials (each of which may be conventional) that are used in its construction, and the desire or otherwise for flexibility, the strip may be from 0.1 to 5 mm thick. Each layer may be from 0.05 to 0.2 mm thick.

Figure 4:
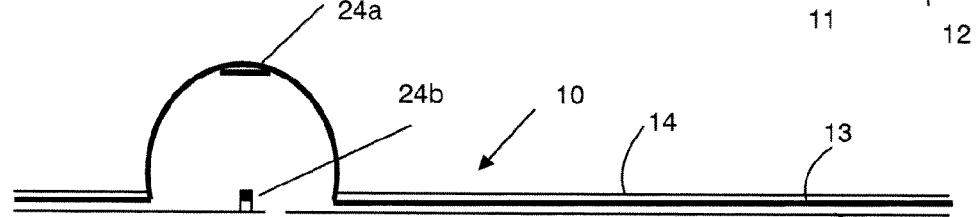

A sensor of the invention may comprise an optical transmitter-receiver or a transceiver, which can be used to accurately measure pressure under a bandage. In the former case, separate circuitry is involved, and in the later case, some part of the circuitry is common to both the transmitter and the receiver. One possible configuration is shown in FIG. 4, which shows a reflective mirror (24a) and a transceiver (24b). One other optical sensing option, appropriate for the under bandage pressure sensing, is to use fibre Bragg grating as the sensor, which is created in a short segment of an optical fibre that reflects particular frequencies of light and transmits others.

A sensor according to the invention is typically designed so that it can be readily connected to an external source of pressure. For this purpose, conventional fittings may be provided, so that the external source can inflate/deflate the pressure-sensing pads independently. The pressure source can be associated with means for determining and/or displaying the pressure applied by a bandage wrapped around the sensor. An external unit comprising a source of pressure may also comprise such measurement/display means, a source of power, control means etc. An indication of the applied pressure may be provided by any suitable display, e.g. a visual display indicating, in association with each pad, an absolute or relative value that is considered to be appropriate and will usually have been pre-determined. The construction and provision of such apparatus, for connection to a sensor of the present invention, will be readily apparent to one of ordinary skill in the art.

Such apparatus should be independent of a single-use sensor of the invention. It can be used in connection with a series of such sensors, for which purpose the connection between the sensor and the apparatus should be readily connectable and releasable.

Accordingly, the device will typically be provided with a manifold allowing connection to the sensing system, so that a series of single-user devices can be used. For example, the device includes air channels communicating along the length of the device to a 'block' at the knee end of the device, and that fit, in turn, to a series of tubes leading to a pressure inflation/deflation device and pressure-sensing system. The design of such a system can be based on well-understood engineering, electronic and software techniques, and needs no further explanation here.

A device of the invention can be constructed in the form of a laminate. One layer can provide independent conduits from one end of the device to the pads. The pads themselves may be provided by a layer of flexible material, e.g. rubber, that can protrude through apertures in a top layer, to form a dome.

It will be readily appreciated that other techniques can be used to produce a devise of the invention. For example, it may be formed by extrusion, with flexible pads added to cover appropriate holes.

Each pad can potentially be controlled, expanded and deflated independently. Deflation (under negative pressure) allows ready removal of the device, after the bandage has been applied.

In use, the pressure can be such that it corresponds to standard graduated compression ranges, defined as Classes I, II and III. The pressure that is applied to the bandage will of course generally be different for each pad. It may typically be in the class ranges, from 15 to 60 mm Hg pressure overall.

A single-use sensor according to the invention can be made simply and economically. Since it is intended for disposal and may come into contact or in proximity of a wound, it will typically be provided in a sterile pack.

The invention will now be described by way of example only with reference to the accompanying drawings.

Figure 1:
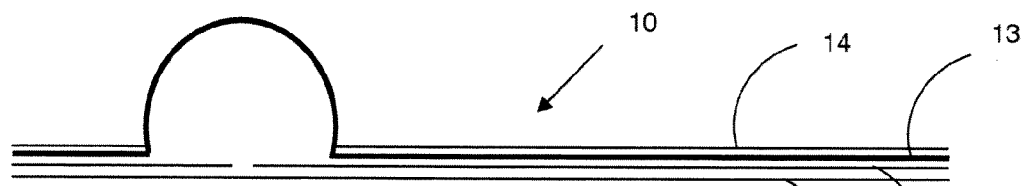
FIG. 1 is a schematic cross-sectional view of a sensor embodying the present invention, illustrating a pad when inflated.

FIG. 1 shows a pneumatic sensor 10 comprising a first or bottom layer 11, a second layer 12, a third layer 13 and a fourth or top layer 14. These layers will now be described in greater detail with reference to FIGS. 6a to 6d.

Figure 6A:
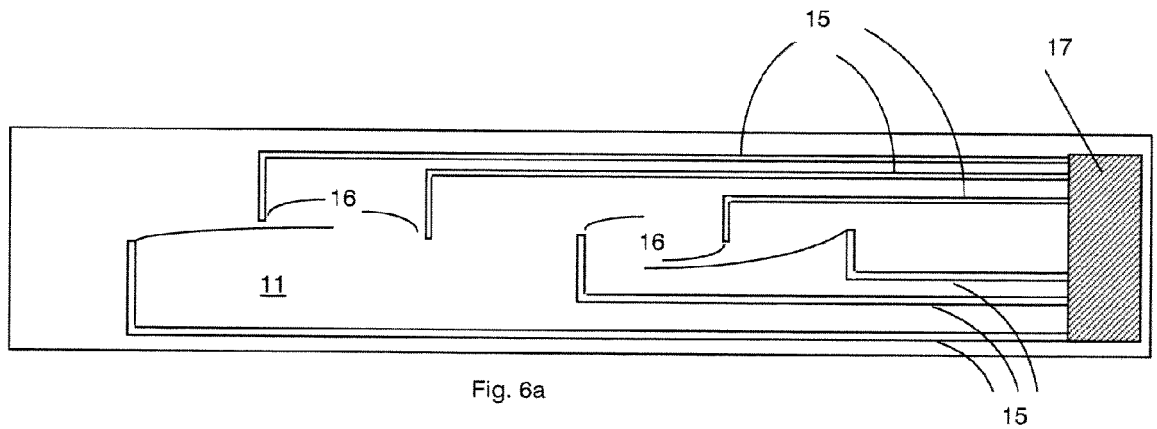
FIGS. 6a, 6b, 6c and 6d are schematic plan views of four separate layers that, when superposed in combination, provide a device of the invention of the type shown (when inflated) in FIG. 1.
Figure 6B:
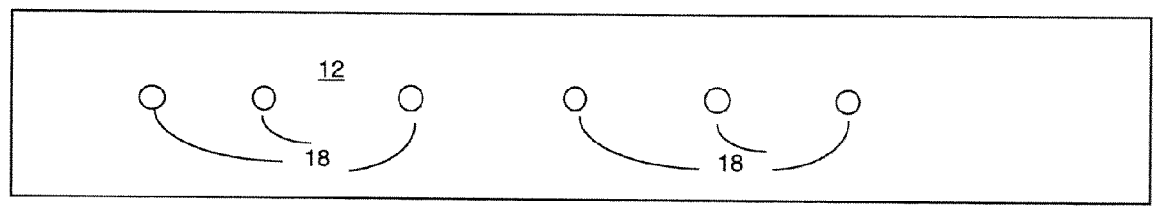

Layer 11 is shown in FIG. 6a, and comprises a plate with channels 15 terminating at points 16 and each connected to a connector 17 adapted (with separate channels) for connection to a source of pressure and a measuring instrument (not shown). The second layer 12 comprises a plurality of air holes 18; their positions correspond to the channel termination points 16. Lamination of the first and second layers means that the channels 15 define conduits from the connector 17 to the air holes 18.

Figure 6C:
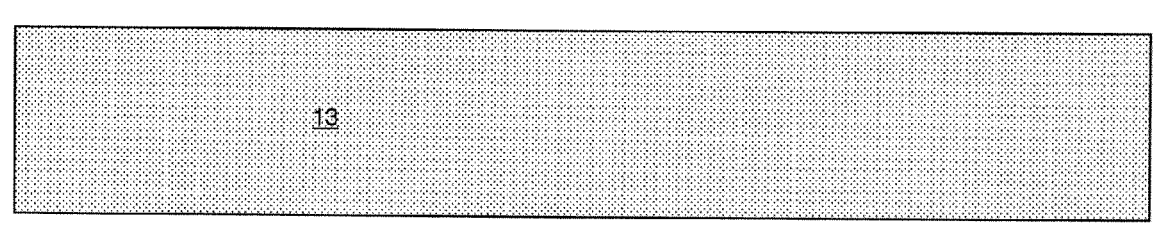
Figure 6D:
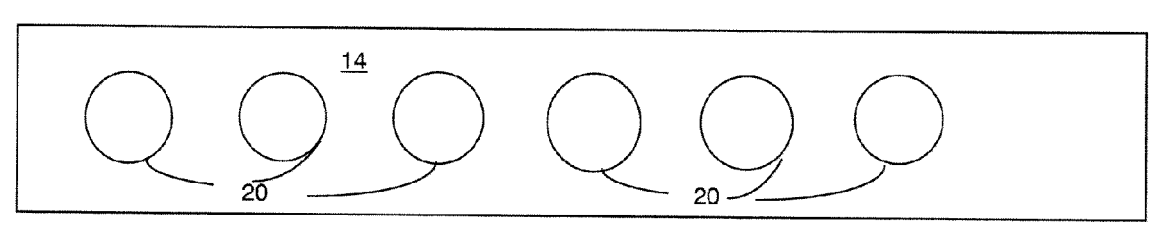

FIG. 6c shows the third layer 13; this is an inflatable diaphragm strip. FIG. 6d shows a top plate 19 including apertures 20 that are larger than and respectively correspond to the apertures 18. When the four layers are superposed and laminated, and air is pumped into the channels in the first layer, the strip 13 is inflated so that a membrane dome is formed by expansion through a hole 20. Such a dome is shown in FIG. 1.

Figure 2:
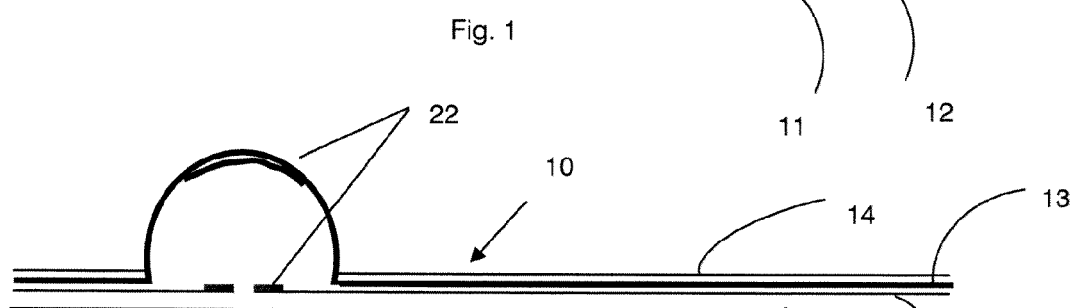
FIGS. 2, 3a, 3b and 4 are further cross-sectional side views of a sensor of the invention, of different embodiments respectively.
Figure 3A:
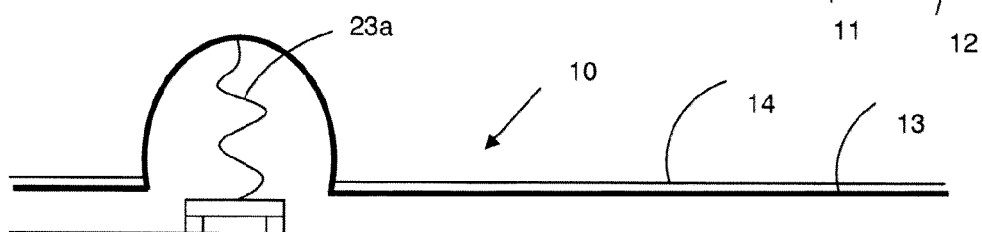
Figure 3B:
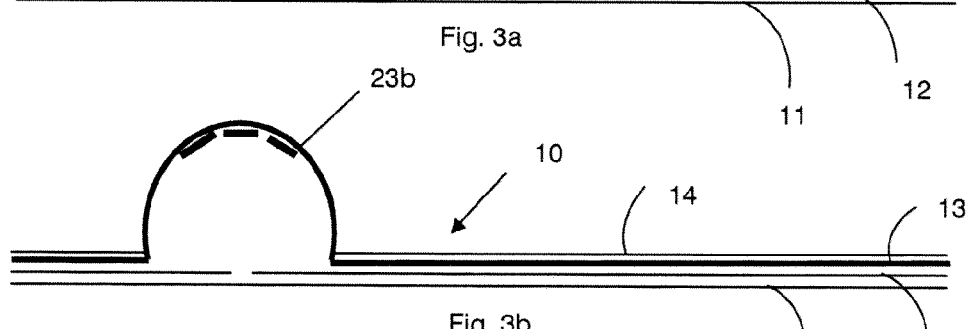
Figure 5:
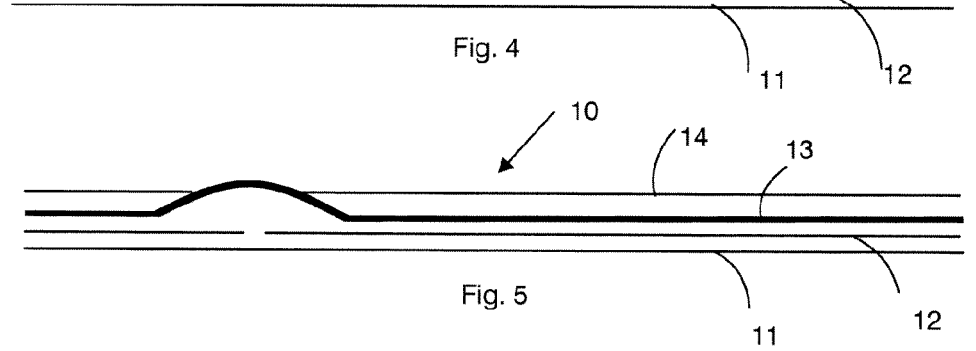
FIG. 5 is a schematic cross-sectional view of part of a device embodying the invention.

Alternative embodiments of the invention are illustrated in FIGS. 2, 3 and 4. As in FIG. 1, the device comprises layers 11, 12, 13 and 14. More specifically, the devices shown in FIGS. 2, 3a, 3b and 4 additionally show, respectively, a capacitative sensor 22, a strain gauge sensor 23a, a strain gauge sensor 23b, and a reflective mirror 24a, and a transceiver 24b. Each of these devices may be used in conjunction with a non-inflatable rubber layer of reduced height, as shown in FIG. 5.

The following Examples illustrate the invention.

Example 1

Pneumatic Sensor

As shown in FIGS. 1 and 6, such a sensor may comprise a laminate of 4 layers, typically 3 of a plastic material and one of rubber. This provides a pneumatic ultra-thin (approx 2 mm), stable, pressure-sensing device. The construction is such that the two bottom layers form an airtight grooved multi-channel trunking. The third layer is the rubber layer and the top plastics layer has apertures through which the rubber can form an inflated dome. Although shown here as a circular dome this may also be elliptical or other shapes. The number and shape of the domes is not critical, but for this example a 6-dome structure is used. The plastics and rubber laminates are essentially oblong in shape, size and length are not limited, but in this example the width is 30 mm and the length 400 mm, with rounded end. The sensing domes are spaced along the length of the oblong section at suitable distances; the actual spacing is not limited, but in this example the spacing is approximately 40 mm. At one end of the sensor unit, a connector block is located to allow access to each individual channel in the grooved construction.

The grooved section has airtight channels running down the length of the sensor unit, individual channels terminating under an appropriate sensing dome. In the area of the termination a small hole is made in a separate layer to allow air from the grooved section to pass through. The rubber diaphragm strip is then stuck to the top of the second layer; areas equal to the sensing dome area are not stuck down. The rubber around the dome area is airtight so the air cannot pass between individual domes or from the domes to the atmosphere. The fourth, plastics layer is then stuck to the topside of the rubber so that the dome shapes in this plastics layer are lined up with the non-stuck areas of the rubber. A connector block is then stuck to one end of the laminated sensor construction, such that pressurised air is allowed to pass from an external unit down each individual channel in the grooved section and to each individual domed area. An alternative option for the sensor construction may be to use not a rubber strip as in 13 but inflatable discrete rubber discs stuck to the top of the second layer; areas equal to the sensing dome area are not stuck down.

In operation, the completed laminated sensor is connected to a remote electronic measuring device that measures pressure via sensing transducers and produces pressurised air to inflate the domes and also for deflating the domes using negative pressure. Pressurised air is then passed through the transducer to the laminated sensor and the individual domes are inflated to a pre-determined level. The inflated domes are now held at this pressure during functional operation of the sensor. The rubber diaphragm material is below the level of the top layer prior to use. As the domes are inflated, the diaphragm material expands above the top layer of plastic to form the sensing dome. By inflating the domes prior to operation, the dynamic hysteresis of the material is reduced, making the monitoring of any changes of pressure on the dome more precise. The changing pressure on the domes is from the bandage's being wound round the patient's leg, with the sensor being placed against the leg prior to the bandaging starting. Once the bandaging is complete, the domes are deflated using a negative pressure generated by the electronic unit, which will ensure that the diaphragm material contracts to below the top layer, to ease removal of the sensor from under the bandage.

This design allows good measurement sensitivity to be achieved, and allows easy removal of the single use sensor from under the bandage, without losing any functional change in the pressure being applied by the bandage to the leg. Some characteristics of this device, for effectiveness are:
1) Pre-inflation prior to use to increase sensitivity
2) De-inflation using negative pressure after use to enable easy removal of the sensor.
3) Ultra-thin thickness
4) Single use device
5) Confidence in getting the correct graduated pressure on the leg every time.
6) Easy to use connection of sensor to electronics and pneumatics.

Example 2

Capacitative Sensor (FIG. 2)

The construction of a capacitive sensor is as for that of Example 1, with the addition of metal plates fixed to a recess in the top layer, and the inside of the dome is metal-coated. Connecting tracks are on the underside of the diaphragm material or in the grooved ducts. Connection to the electronics unit is via the connection block.

In operation, the diaphragm is inflated as per the pneumatic version. As the dome expands, the distance from the metal plates on the top layer and the metal on the inside of the dome changes, giving a change in capacitance value. The area of the metal inside the dome would also change, giving additional capacitance change. Once the capacitance value has stabilised (dome fully inflated), then any change in the dome shape would show a measurable change in capacitance. These changes will have a relationship to the pressure that is changing the dome's shape, and can be calibrated to give a linear relationship. On completion of the measurement, the dome is deflated, as in the pneumatic sensor.

Example 3

Strain Gauge Sensor (FIG. 3)

Construction of a strain gauge sensor is as for that of Example 2, but with a strain gauge fitted in place of the capacitor plates on the top layer and the centre of the dome attached to the centre of the stain gauge. Two possible versions of the strain gauge are shown in FIGS. 3a and 3b.

In operation, as the dome is inflated, the centre of the strain gauge is pulled up (3a), changing the strain gauge resistance.

When the dome is fully inflated, applied external pressure on the dome will cause changes on the strain gauge proportional to the pressure applied.

An alternative is to coat the inside of the dome (3b) with a conductive element and this would then become the strain gauge. Again, any change with the inflated dome shape due to external pressure would cause changes to the conductive coating and therefore its resistance. This can then be calibrated to form a relationship between pressure and resistance.

Example 4

Optical Sensor (FIG. 4)

Construction is as in Examples 2 and 3, except that the strain gauge is replaced by an optical transceiver with the reflective mirror inside the dome. As the dome is inflated, the distance between transceiver and reflector changes; this can be monitored externally to produce a relationship between distance and pressure. Once the dome is fully inflated then an external pressure will change the dome shape and cause optical path changes.

Example 5

Non-inflatable Semi-Rigid Sensor (FIG. 5)

Manufactured in a similar way to the device of other Examples, but without the diaphragm. In this version, the top sheet is a thinned semi-rigid dome shape to which pressure may be may applied. In this device there will be a very small bulge and different types of sensors (2-4) can be implemented. This device has only three laminate layers.

In addition to the methods of sensing described above, this type of semi-rigid construction and also the inflatable type can be readily used in conjunction with piezoelectric, magnetic, inductive, electrostatic and electromagnetic sensing.

A study has been designed to test the efficacy of a sensor of the invention, in the treatment of ulcers.

Study

The lower limb of a patient with an area of (venous) ulceration suitable for graduated compression bandaging (using either 3-layer, or 4-layer systems as described elsewhere and as part of routine clinical management) has the ulcer site cleaned and topically dressed. A single use, disposable sensor of the invention is pre-inflated, to raise the profile of the (4-6) incorporated pressure sensing 'balloons'. The pressure in the device is maintained at a steady state and is calibrated at this point to read 'zero'.

The sensor is placed vertically, lying on the outer aspect of the calf, such that its lower aspect is at the level of the upper part of the lateral malleolus (outer part of the ankle 'bone'). Bandaging commences from the forefoot, passing up towards the knee, in a standard fashion, and over the pressure sensor. Three or four layers of bandaging are applied—the bandages themselves are elasticated and heavy duty. Ideally, the bandages are applied such that the pressure sensed at the level of the ankle will be approximately 40 mmHg, declining to approximately 30 mmHg at the knee—with a progressive and steady fall of pressures sensed in the interval between, to provide 'graduated' compression moving up the calf. The pressure sensors require an accuracy (tolerance) of no greater than 2 mmHg.

The invention claimed is:

1. A sensor for measuring pressure applied by a bandage, the sensor comprising:
    an elongate strip having a plurality of pads arranged along its length, and
    a connection to each pad, whereby pressure applied to each pad can be determined independently with the connection,
    wherein each pad is inflatable so as to form an expanded pad protruding above the surface of the strip, and also deflatable so that it does not impede removal of the sensor from the bandage.

2. The sensor according to claim 1, wherein each pad includes a strain gauge.

3. The sensor according to claim 1, wherein each pad includes a capacitance sensor for measuring the pressure in each inflated pad.

4. The sensor according to claim 1, wherein each pad includes an optical sensor for measuring the pressure in each inflated pad.

5. The sensor according to claim 1, further comprising conduit to each pad by which each pad is independently inflatable.

6. A sterile pack containing a sensor according to claim 5.

7. A method for testing the compression of a bandage around a limb, the method comprising,
    positioning a sensor, according to claim 1, along the length of a limb;
    winding the bandage around the limb and the sensor, and
    determining the pressure applied to the sensor so as to determine the amount of compression applied to the limb by the bandage.

8. The method according to claim 7, further comprising:
    inflating each pad in sequence,
    determining the pressure applied to the limb at each corresponding point,
    deflating each pad, and
    removing the sensor from the bandage.

* * * * *

UNITED STATES PATENT AND TRADEMARK OFFICE
CERTIFICATE OF CORRECTION

| | |
|---|---|
| PATENT NO. | : 9,204,799 B2 |
| APPLICATION NO. | : 13/977385 |
| DATED | : December 8, 2015 |
| INVENTOR(S) | : Roy F. Davies et al. |

It is certified that error appears in the above-identified patent and that said Letters Patent is hereby corrected as shown below:

In the claims,

Column 8, Claim 5,
Line 1, "comprising conduit" should read --comprising a conduit--.

Signed and Sealed this
Seventeenth Day of May, 2016

Michelle K. Lee
*Director of the United States Patent and Trademark Office*